(12) United States Patent
Kim

(10) Patent No.: US 11,433,003 B2
(45) Date of Patent: Sep. 6, 2022

(54) INTERNAL HOLE FILLER OF ABUTMENT FOR IMPLANT

(71) Applicant: Jae Young Kim, Seoul (KR)

(72) Inventor: Jae Young Kim, Seoul (KR)

(*) Notice: Subject to any disclaimer, the term of this patent is extended or adjusted under 35 U.S.C. 154(b) by 430 days.

(21) Appl. No.: 16/642,394

(22) PCT Filed: Aug. 27, 2018

(86) PCT No.: PCT/KR2018/009876
§ 371 (c)(1),
(2) Date: Feb. 27, 2020

(87) PCT Pub. No.: WO2019/066267
PCT Pub. Date: Apr. 4, 2019

(65) Prior Publication Data
US 2020/0188238 A1    Jun. 18, 2020

(30) Foreign Application Priority Data

Sep. 29, 2017   (KR) .................. 10-2017-0127025

(51) Int. Cl.
*A61K 6/58*          (2020.01)
(52) U.S. Cl.
CPC ..................................... *A61K 6/58* (2020.01)
(58) Field of Classification Search
CPC ..................................................... A61K 6/58
See application file for complete search history.

(56) References Cited

U.S. PATENT DOCUMENTS

| 4,531,916 | A | * | 7/1985 | Scantlebury | ............. | A61C 8/00 433/176 |
| 5,165,893 | A | | 11/1992 | Thompson | | |
| 2004/0067467 | A1 | | 4/2004 | Gault | | |

FOREIGN PATENT DOCUMENTS

| KR | 10-2010-0130178 | 12/2010 |
| KR | 20-2014-0005818 | 11/2014 |
| KR | 10-2017-0020728 | 2/2017 |

OTHER PUBLICATIONS

Osvaldo D. Moraguez, et al., "The Use of Polytetrafluoroethylene Tape for the Management of Screw Access Channels in Implant-Supported Prostheses", The Journal of Prosthetic Dentistry, Mar. 2010, vol. 103, Issue 3, pp. 189-191.
International Search Report and Written Opinion of the ISA for PCT/KR2018/009876 dated Nov. 13, 2018, 9 pages.

* cited by examiner

*Primary Examiner* — Michael P Cohen
(74) *Attorney, Agent, or Firm* — Nixon & Vanderhye, P.C.

(57) ABSTRACT

The present invention relates to an internal hole filler of an abutment for implant, which includes first polytetrafluoroethylene (first PTFE) and second polytetrafluoroethylene (second PTFE), wherein tensile strength measured after sintering the first PTFE is in a range of 20 MPa or more to less than 28 MPa, and tensile strength measured after sintering the second PTFE is 28 MPa or more, and a method of filling an internal hole of the abutment for implant.

9 Claims, 1 Drawing Sheet

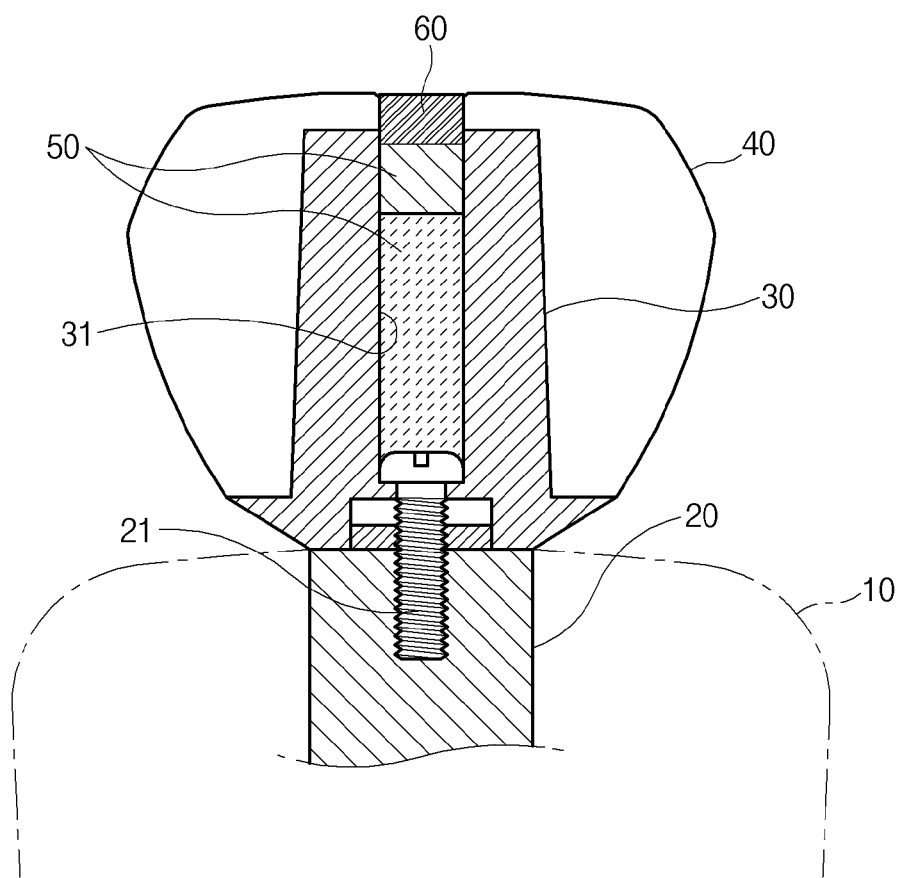

INTERNAL HOLE FILLER OF ABUTMENT FOR IMPLANT

CROSS-REFERENCE TO RELATED APPLICATIONS

The present application is a national phase entry under 35 U.S.C. § 371 of International Application No. PCT/KR2018/009876 filed Aug. 27, 2018, the disclosure of which is incorporated herein in its entirety by reference, which claims priority to Korean Patent Application No. 2017-0127025, filed on Sep. 29, 2017, in the Korean Intellectual Property Office, the disclosure of which is incorporated herein in its entirety by reference.

TECHNICAL FIELD

The present invention relates to an internal hole filler of an abutment for implant.

BACKGROUND ART

In general, an implant refers to a replacement that restores when tissue is lost, but, in dentistry, it means implantation of artificial teeth. Specifically, it is a procedure to restore the function of teeth by implanting a fixture made of titanium or the like, which is not rejected by the human body, into bone from which the tooth is missing so as to replace root of the missing tooth and then fixing an artificial tooth called a crown.

Such a dental implant, as illustrated FIG. 1, includes a fixture 20 supporting a crown 40 by being implanted in alveolar bone 10 in a missing tooth area, such as root of natural tooth, an abutment 30 connecting the fixture 20 and the crown 40, a screw 21 for fastening the abutment 30 to the fixture 20, and the crown 40 which is fixed in the mouth by the abutment 30 and is designed to reproduce the same shape and function as natural teeth.

The fixture 20 is osseointegrated so as to be completely fixed to the alveolar bone 10 as the root of natural tooth, the abutment 30 is connected to the fixture 20 of the implant with the screw 21 after the osseointegration, and the implant is completed when the crown 40 is mounted thereon.

In this case, a hole 31 is formed at the center of the abutment 30, and the abutment 30 may be fixed to an upper end of the fixture 20 by inserting the screw 21 through the hole 31 and screwing the screw 21 into the fixture 20. The crown 40 is placed on an outer side of the abutment 30 and integrally fixed thereto. In this case, in order to prevent loosening of the abutment 30 during the mounting of the crown 40, a filler 50, such as cotton or silicon, is placed in the internal hole 31 of the abutment 30, and a resin 60 is injected into an uppermost opening to seal the opening.

Since the filler 50 and the screw 21 of the fixture 20 are in contact with each other in a conventional dental implant, a bite force applied to the crown 40 in the process of chewing food is transmitted to the filler 50 and is directly transmitted to the screw 21 through the filler, and thus, a problem occurs in which the screw 21 is loosened by the bit force. In order to retighten the loose screw 21, the screw 21 may be tightened after the resin 60 is removed and the filler 50 in the holes 31 of the abutment 30 is completely taken out.

Gauze, cotton, resin, or silicon has been used as the hole filler 50 of a conventional abutment for implant. However, in a case in which gauze or cotton is used as the hole filler, the gauze or cotton may cause bacterial growth and malodor when it is contaminated with saliva, and, in a case in which the hole of the abutment is not completely filled, it is disadvantageous in that the gauze or cotton may not support the resin 60 formed thereon. Also, in a case in which silicon is used as the hole filler, there are limitations in that it is not easy to insert the silicon into the hole of the abutment due to elasticity of the silicon and the silicon does not sufficiently support the resin 60 as the length of the silicon increases. Furthermore, in a case in which a resin is used as the hole filler, since the resin is very hard at room temperature, it must be used after being softened by applying heat. Thus, it is disadvantageous in that a restoration process is complicated, restoration takes a long time, and leakage may occur in a restored portion because contraction may occur during a polymerization process. In addition, since the resin is expensive, there is also a concern that costs may increase when the inside of the hole is filled with the resin. Also, since it is difficult to completely remove the gauze, cotton, resin, or silicon, it remains in the hole 31 as a residue, and thus, there is a limitation in that it may interfere with the operation of the screw 21.

Therefore, there is a need to develop a hole filler of an abutment for implant which may tightly fill a hole of the abutment and is easy to be removed.

DISCLOSURE OF INVENTION

Technical Problem

An aspect of the present invention provides an internal hole filler of an abutment for implant which may be easily inserted and removed and may tightly fill the inside of the abutment for implant.

Another aspect of the present invention provides a method of filling an internal hole of the abutment for implant.

Another aspect of the present invention provides an abutment for implant which includes the internal hole filler of the abutment for implant.

Another aspect of the present invention provides an implant including the abutment for implant.

Solution to Problem

According to an aspect of the present invention, there is provided an internal hole filler of an abutment for implant, which is inserted into an internal hole of the abutment for implant, including: first polytetrafluoroethylene (first PTFE) and second polytetrafluoroethylene (second PTFE), wherein tensile strength measured after sintering the first PTFE is in a range of 20 MPa or more to less than 28 MPa, and tensile strength measured after sintering the second PTFE is 28 MPa or more.

According to another aspect of the present invention, there is provided a method of filling an internal hole of an abutment for implant which includes: disposing an internal hole filler of an abutment for implant, which includes first polytetrafluoroethylene (first PTFE) and second polytetrafluoroethylene (second PTFE), in inside of a hole of the abutment for implant; and filling the inside of the hole with the hole filler by pressurizing the hole filler using an implant device, wherein tensile strength measured after sintering the first PTFE is in a range of 20 MPa or more to less than 28 MPa, and tensile strength measured after sintering the second PTFE is 28 MPa or more.

Advantageous Effects of Invention

Since a filler of the present invention includes two kinds of polytetrafluoroethylene with different tensile strengths, ductility and hardness are properly adjusted so that the filler may be easily filled even with a small force when being inserted into a hole of an abutment for implant and the filler may be easily removed without breaking when subsequently removed from the hole of the abutment.

Also, since the polytetrafluoroethylene has excellent safety, it is applicable to the human body as a dental restorative material.

BRIEF DESCRIPTION OF DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

FIG. 1 is a cross-sectional view of a conventional dental implant.

BEST MODE FOR CARRYING OUT THE INVENTION

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Gauze, cotton, resin, and silicon have been studied as a conventional internal hole filler of an abutment for implant. However, it was difficult to completely fill an internal hole of the abutment with the gauze, cotton, resin, and silicon. Particularly, with respect to the resin, since photopolymerization is essential during filling, time and costs may be increased. Also, in a case in which these materials are removed from the internal hole of the abutment, it is disadvantageous in that residues may remain in the hole.

In order to address these limitations, there have been attempts to use polytetrafluoroethylene (PTFE) with excellent stability as a filler. However, in a case in which PTFE with excellent ductility was used alone, it was possible to tightly fill the inside of the hole with the PTFE, but it was not easy to completely remove the PTFE from the inside of the hole. In contrast, in a case in which PTFE with excellent stiffness was used alone, it was easy to remove the PTFE from the inside of the hole, but it was not easy to tightly fill the inside of the hole using the PTFE.

Thus, the present inventors found that an internal hole filler of an abutment for implant, which not only easily fill but is also easily removed, may be prepared by using and mixing two kinds of PTFE with different tensile strengths, thereby leading to the completion of the present invention.

Specifically, with respect to a hole filler of the present invention which is inserted into an internal hole of the abutment for implant, the hole filler includes first polytetrafluoroethylene (first PTFE) and second polytetrafluoroethylene (second PTFE), wherein tensile strength measured after sintering the first PTFE is in a range of 20 MPa or more to less than 28 MPa, and tensile strength measured after sintering the second PTFE is 28 MPa or more.

A filler, in which ductility and hardness are properly adjusted, may be provided by using the two kinds of PTFE with different tensile strengths as described above, and filling property and removing property may be improved by properly adjusting the ductility and the hardness.

Also, in a case in which the two kinds of PTFE with different tensile strengths are used, since molding is easy, a filler having a small diameter may be easily prepared.

The first PTFE may have a tensile strength, which is measured after sintering the first PTFE, of 20 MPa or more to less than 28 MPa, preferably 20 MPa or more to 27.4 MPa, and more preferably 20.7 MPa to 27.4 MPa. In a case in which the tensile strength of the first PTFE satisfies the above range, since the first PTFE exhibits excellent ductility, the first PTFE may tightly fill the internal hole when the first PTFE is pressurized by using an implant device after the first PTFE is disposed in the internal hole of the abutment. However, in a case in which the tensile strength of the first PTFE is less than 20 MPa, since the ductility is excessively increased, removal from the inside of the abutment is not easy and, accordingly, it is disadvantageous in that time required for implant is increased.

The expression "tensile strength" denotes a value obtained by dividing the maximum load until a material breaks by a cross-sectional area of parallel portion of a specimen, that is, maximum tensile stress per unit area. The higher the tensile strength value is, the higher the strength of the material is.

The implant device denotes a device for inserting and removing the filler into and from the internal hole of the abutment for implant, wherein it may preferably include a portion having a hook shape on one side of both ends of a rod and a portion having a mortar shape on the opposite end. Specifically, the filler may be tightly inserted into the internal hole of the abutment by pressurizing the filler with the portion having a mortar shape, and the filler may be removed from the internal hole of the abutment by using the portion having a hook shape.

The second PTFE may have a tensile strength, which is measured after sintering the second PTFE, of 28 MPa or more, preferably 28 MPa to 35 MPa, and more preferably 28 MPa to 30 MPa. In a case in which the tensile strength of the second PTFE is within the above range, since the second PTFE has excellent strength, the second PTFE does not break even if a force is applied thereto using the implant device, and thus, the removal of the second PTFE from the internal hole of the abutment for implant is easy. For example, in a case in which the tensile strength of the second PTFE is less than 28 MPa, since the strength is reduced and ductility is increased, the second PTFE may be easily deformed or broken even if a small force is applied. In a case in which the tensile strength of the second PTFE is greater than 35 MPa, since the ductility of the second PTFE is reduced, its shape does not change even if a force is applied, and thus, it is difficult to apply the second PTFE as the internal hole filler of the abutment for implant.

The tensile strength of the PTFE may be measured according to ISO 12086. Specifically, dried PTFE powder is put in a circular mold and pressure-molded at a temperature of 100° C. to 400° C. to prepare a molded article, and the molded article is then removed from the mold and maintained at room temperature and a relative humidity of 40% to 60% for 10 hours to 30 hours. Thereafter, a specimen, which is prepared by cutting the molded article to a desired size, is placed in a tensile tester, and the tensile strength of the PTFE may then be measured.

The hole filler according to the present invention may include the first PTFE and the second PTFE in a weight ratio of (30:70) to (70:30), for example, (40:60) to (60:40).

In a case in which the first PTFE and the second PTFE are included in the above weight ratio, the first PTFE and the second PTFE may tightly fill the internal hole of the abutment for implant due to excellent deformability and may be removed without breaking due to excellent strength during the subsequent removal. Accordingly, a filler, which may be easily inserted and removed into and from the internal hole of the abutment, may be provided.

For example, the hole filler may be prepared by the steps of: aging in which a lubricant is added to mixed powder, in which the first PTFE powder and the second PTFE powder are mixed in a weight ratio of (30:70) to (70:30), and the mixed powder is maintained for a predetermined time to allow the lubricant to permeate the mixed powder; and pressing and injection molding the mixed powder.

The lubricant is to agglomerate the first PTFE powder and the second PTFE powder while uniformly mixing them, wherein various lubricants used in the art may be used without limitation.

The hole filler according to the present invention may have a cylindrical shape having a length of 5 mm to 80 mm and a diameter of 0.10 to 3Φ.

Preferably, the length of the hole filler may be greater than a length of the internal hole of the abutment for implant. More preferably, the length of the hole filler may be about 100% to 150% based on the length of the internal hole of the abutment for implant. For example, the hole filler may be cut so that the length of the hole filler is 100% to 150%, for example, 130% to 150% of the length of the internal hole of the abutment for implant and may then be used.

Also, the diameter of the hole filler may preferably be smaller than a diameter of the internal hole of the abutment for implant. More preferably, the diameter of the hole filler may be about 70% to 99% based on the diameter of the internal hole of the abutment for implant. For example, the diameter of the internal hole of the abutment for implant may be in a range of 1φ to 3.3φ, for example, 2φ to 3.1φ, and the diameter of the hole filler may be in a range of 0.1 Φ to 3Φ, for example, 1 Φ to 2.5Φ. In this case, the unit "Φ" of the diameter means mm.

Furthermore, the present invention provides a method of filling an internal hole of an abutment for implant which includes the steps of: disposing an internal hole filler of an abutment for implant, which includes first polytetrafluoroethylene (first PTFE) and second polytetrafluoroethylene (second PTFE), in inside of a hole of the abutment for implant; and filling the inside of the hole with the hole filler by pressurizing the hole filler using an implant device, wherein tensile strength measured after sintering the first PTFE is in a range of 20 MPa or more to less than 28 MPa, and tensile strength measured after sintering the second PTFE is 28 MPa or more.

In the present invention, the hole filler including the two kinds of PTFE with different tensile strengths is prepared to have appropriate length and diameter and is then disposed in the inside of the hole of the abutment for implant. The hole filler according to the present invention may preferably have a length of about 100% to 150% and a diameter of about 70% to 99% based on the length and diameter of the internal hole of the abutment for implant. In this case, the hole filler, for example, may be molded to have appropriate length and diameter by injection molding.

After the hole filler is disposed in the internal hole of the abutment, the hole filler may be tightly inserted into the internal hole of the abutment by pressurizing the hole filler using the implant device.

Also, the present invention provides an abutment for implant which includes the internal hole filler of the abutment for implant.

Any abutment for implant conventionally used in the art may be used as the abutment for implant without limitation, and the internal hole of the abutment for implant may be filled using the filler according to the present invention.

Furthermore, the present invention provides an implant including the abutment for implant in which the internal hole is filled with the filler as described above.

MODE FOR THE INVENTION

Hereinafter, the present invention will be described in detail, according to specific examples. The invention may, however, be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

DuPont™ Teflon 669-N (tensile strength: 20.7 MPa~27.4 MPa) was used as first polytetrafluoroethylene (first PTFE), and 3M Dyneon TF2021Z (tensile strength: 28 MPa) was used as second polytetrafluoroethylene (second PTFE). The first PTFE and the second PTFE were mixed in a weight ratio of 48.5:51.5 to prepare mixed PTFE powder. Subsequently, the mixed PTFE powder was added to a lubricant and aged, and the mixed PTFE powder thus aged was pressed and injection molded to prepare an internal hole filler of an abutment for implant.

Comparative Example 1

Silicon was used as an internal hole filler of an abutment for implant.

Comparative Example 2

A resin was used as an internal hole filler of an abutment for implant.

Comparative Example 3

An internal hole filler of an abutment for implant was prepared in the same manner as in Example 1 except that 100% of DuPont™ Teflon 669-N was used.

Comparative Example 4

An internal hole filler of an abutment for implant was prepared in the same manner as in Example 1 except that 100% of 3M Dyneon TF2021Z was used.

Experimental Example: Internal Hole Filling and Removal Test of Abutment for Implant An internal hole of an abutment for implant was filled with each of the filler prepared in Example 1 and Comparative Examples 1 to 4 at room temperature (25° C.). After it was maintained for one week, the filler was removed, and the results thereof are presented in Table 1 below.

During the filling test, a case where filling was possible within 1 minute was indicated by "⊚", a case where filling was possible for more than 1 minute to 10 minutes or less was indicated by "O", a case where filling was possible for more than 10 minutes to 20 minutes or less was indicated by "Δ", and a case where filling took 20 minutes or more was indicated by "X".

Also, during the removal test, a case where the filler was completely removed from the internal hole within 2 times was indicated by "⊚", a case where the filler was completely removed within 5 times was indicated by "O", a case where 10 times or more were required was indicated by "Δ", and a case where the filler was broken during removal was indicated by "X".

TABLE 1

|  | Filling test | Removal test |
| --- | --- | --- |
| Example 1 | ⊚ | ⊚ |
| Comparative Example 1 | X | ⊚ |
| Comparative Example 2 | X | X |
| Comparative Example 3 | ⊚ | Δ |
| Comparative Example 4 | Δ | ⊚ |

As illustrated in Table 1, with respect to the hole filler of Example 1, filling in the internal hole was possible within 1 minute due to deformability, and removal of the filler from the internal hole of the abutment was also easy.

However, with respect to Comparative Example 1 in which the silicon was used as the hole filler, removal of the silicon was easy due to elasticity of the silicon, but, since the silicon did not have deformability, it was not possible to tightly fill the hole with the silicon. Also, in a case in which the resin was used as the hole filler as in Comparative Example 2, it was not possible to fill the hole with the resin because the resin was hard at room temperature. Since the resin may be used after photopolymerization by applying heat, filling time took 20 times or more longer than that of Example 1. Furthermore, since the internal hole was filled with the resin while the resin was cured by heat, the resin was adhered to a wall of the internal hole. Thus, removal of the resin was also not easy and residues remained in the hole of the abutment after the removal. In a case in which the PTFE having a tensile strength of 20.7 MPa to 27.4 MPa was used alone as the hole filler as in Comparative Example 3, the hole of the abutment may be tightly filled within 1 minute due to excellent ductility, but it was not easy to remove the hole filler from the inside of the abutment. Also, in a case in which the PTFE having a tensile strength of 28 MPa was used alone as the hole filler as in Comparative Example 4, since the strength was excellent, removal of the hole filler was easy, but, since ductility was low, filling time took about 10 times longer than that of Example 1.

DESCRIPTION OF THE SYMBOLS

10: Alveolar bone
20: Fixture
21: Screw
30: Abutment
31: Internal hole of the abutment
40: Crown
50: Filler
60: Resin

The invention claimed is:

1. An internal hole filler of an abutment for implant which is inserted into an internal hole of the abutment for implant, the hole filler comprising:
   wherein the hole filler includes a first polytetrafluoroethylene (first PTFE) and a second polytetrafluoroethylene (second PTFE),
   wherein tensile strength measured after sintering the first PTFE is in a range of 20 MPa or more to less than 28 MPa, and tensile strength measured after sintering the second PTFE is 28 MPa or more.

2. The internal hole filler of an abutment for implant of claim 1, wherein the first PTFE and the second PTFE are included in a weight ratio of (30:70) to (70:30).

3. The internal hole filler of an abutment for implant of claim 1, wherein a diameter of the hole filler is smaller than a diameter of the internal hole of the abutment for implant.

4. The internal hole filler of an abutment for implant of claim 1, wherein the hole filler has a diameter of 0.1 φ to 3 φ.

5. The internal hole filler of an abutment for implant of claim 1, wherein a length of the hole filler is greater than a length of the internal hole of the abutment for implant.

6. The internal hole filler of an abutment for implant of claim 1, wherein the hole filler has a length of 5 mm to 80 mm.

7. A method of filling an internal hole of an abutment for implant, the method comprising:
   disposing an internal hole filler of an abutment for implant, which includes first polytetrafluoroethylene (first PTFE) and second polytetrafluoroethylene (second PTFE), in inside of a hole of the abutment for implant; and
   filling the inside of the hole with the hole filler by pressurizing the hole filler using an implant device,
   wherein tensile strength measured after sintering the first PTFE is in a range of 20 MPa or more to less than 28 MPa, and tensile strength measured after sintering the second PTFE is 28 MPa or more.

8. An abutment for implant, the abutment comprising the hole filler of claim 1.

9. An implant comprising the abutment for implant of claim 8.

* * * * *